(12) United States Patent
Ohashi et al.

(10) Patent No.: US 9,901,094 B2
(45) Date of Patent: Feb. 27, 2018

(54) ANTIBACTERIAL RESIN COMPOSITION

(71) Applicant: TOYO SEIKAN GROUP HOLDINGS, LTD., Tokyo (JP)

(72) Inventors: Kazuaki Ohashi, Kanagawa (JP);
Yasuhiro Kosaka, Kanagawa (JP);
Akiko Ogata, Kanagawa (JP);
Takahiro Kawakami, Osaka (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 0 days.

(21) Appl. No.: 15/153,116

(22) Filed: May 12, 2016

(65) Prior Publication Data
US 2016/0249605 A1    Sep. 1, 2016

Related U.S. Application Data

(62) Division of application No. 13/984,366, filed as application No. PCT/JP2012/053411 on Feb. 14, 2012, now Pat. No. 9,363,993.

(30) Foreign Application Priority Data

Feb. 15, 2011   (JP) .................................. 2011-030118

(51) Int. Cl.
| | | |
|---|---|---|
| *A01N 25/34* | (2006.01) | |
| *A01N 43/80* | (2006.01) | |
| *A01N 59/16* | (2006.01) | |
| *A01N 25/10* | (2006.01) | |
| *C08K 5/3417* | (2006.01) | |
| *C08K 5/353* | (2006.01) | |
| *C08K 5/46* | (2006.01) | |
| *C08K 5/00* | (2006.01) | |
| *A01N 55/02* | (2006.01) | |

(52) U.S. Cl.
CPC ............. *A01N 25/10* (2013.01); *A01N 25/34* (2013.01); *A01N 43/80* (2013.01); *A01N 55/02* (2013.01); *A01N 59/16* (2013.01); *C08K 5/0058* (2013.01); *C08K 5/3417* (2013.01); *C08K 5/353* (2013.01); *C08K 5/46* (2013.01)

(58) Field of Classification Search
None
See application file for complete search history.

(56) References Cited

U.S. PATENT DOCUMENTS

| | | | |
|---|---|---|---|
| 3,997,346 A | 12/1976 | Masuda et al. | |
| 4,859,241 A * | 8/1989 | Grundy ................... C03C 8/18 | 106/1.14 |
| 8,106,228 B2 | 1/2012 | Ohashi et al. | |
| 8,361,553 B2 | 1/2013 | Karandikar et al. | |
| 2007/0003603 A1 | 1/2007 | Karandikar et al. | |
| 2007/0207335 A1 | 9/2007 | Karandikar et al. | |
| 2007/0254044 A1 | 11/2007 | Karandikar et al. | |
| 2010/0221486 A1 | 9/2010 | Nonninger et al. | |
| 2010/0229314 A1 * | 9/2010 | Takiguchi ............. A61K 8/442 | 8/405 |

FOREIGN PATENT DOCUMENTS

| | | |
|---|---|---|
| EP | 1941797 | 7/2008 |
| JP | 62-000404 | 1/1987 |
| JP | 03-206009 | 9/1991 |
| JP | 11-158051 | 6/1999 |
| JP | 2008-508321 | 3/2008 |
| JP | 2010-248124 | 11/2010 |
| WO | 2006/015317 | 2/2006 |
| WO | 2008/69034 | 6/2008 |

OTHER PUBLICATIONS

International Search Report for PCT/JP2012/053411, dated May 22, 2012.
E.P.O. Office action, dated Aug. 26, 2014.

* cited by examiner

*Primary Examiner* — Abigail Vanhorn
(74) *Attorney, Agent, or Firm* — Greenblum & Bernstein, P.L.C.

(57) ABSTRACT

An antibacterial resin composition comprising a thermoplastic resin or a thermosetting resin blended with at least one kind of fatty acid metal salt selected from Ag, Cu, Zn, Co and Ni, and a compound represented by the following formula (2):

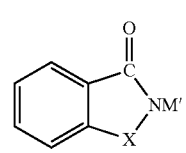

(2)

wherein M' is any one of Na, K or H, and X is an atom selected from C, O, S and P, or an atomic group thereof.

2 Claims, 1 Drawing Sheet

ANTIBACTERIAL RESIN COMPOSITION

The present application is a divisional of pending U.S. patent application Ser. No. 13/984,366, which is a National Phase of PCT/JP2012/053411 filed Feb. 14, 2012 and claims the benefit of Japanese Application No. JP 2011-030118 filed Feb. 15, 2011, the disclosures of which are incorporated by reference herein in their entireties.

TECHNICAL FIELD

This invention relates to an antibacterial resin composition and, more specifically, to an antibacterial resin composition which permits antibacterial substances such as silver and the like made present in the resin to efficiently elute out and the eluted metals to remain stable as ions thereof so that excellent antibacterial power can be exhibited.

BACKGROUND ART

In recent years, a variety of antibacterial compositions have been proposed for use in public places such as straps, for use as materials related to the houses such as wall papers and furnishings, for use as filters of the air conditioners and, further, for use as various products such as stationeries that require antibacterial property in addition to being used for the products such as medical supplies and containers that are used under high-temperature and highly humid conditions like in a kitchen, bath room and toilet room where germs and molds can easily multiply.

For example, the following patent document 1 discloses a composition containing a solvent, silver nano-particles and a stabilizer, and the following patent document 2 discloses an antibacterial composition containing an organosilver type antibacterial agent and an organic antibacterial agent.

The present inventors have proposed already a resin composition (patent document 3) containing ultrafine metal particles having an organic acid component on the surfaces of the ultrafine metal particles as the resin composition that is capable of immunologically inactivating allergenic substances consisting of plant proteins such as cedar pollen and the like and animal proteins such as ticks, excrements thereof, molds and the like.

PRIOR ART DOCUMENTS

Patent Documents

Patent document 1: JP-T-2008-508321
Patent document 2: JP-A-2010-248124
Patent document 3: International Publication WO2008/69034

OUTLINE OF THE INVENTION

Problems that the Invention is to Solve

The composition disclosed in the above patent document 1 comprises a dispersion solution which is obtained by dispersing silver nano-particles in a solvent, and is used to impart antibacterial property by bringing the dispersion solution into contact with the surface of the base body to which the antibacterial property is to be imparted. Therefore, the dispersion solution cannot be fixed to the base body to a sufficient degree, and is not still fully satisfactory in regard to sustaining the effect thereof.

The compositions disclosed in the patent documents 2 and 3 are not the ones that are to be used being applied onto the formed article that has been formed in advance unlike that of the patent document 1, but are the ones used in combination with a resin to impart antibacterial property to the formed article of the resin, offering advantage from the standpoint of productivity and sustenance of the effect.

From the economical point of view, however, it has been desired that these antibacterial resin compositions, too, exhibit antibacterial property comparable to or superior to those of the conventional property but using expensive substances such as silver and the like in amounts less than the amounts used so far, yet maintaining excellent antibacterial property.

Namely, in order for the antibacterial resin composition to exhibit antibacterial effect, it is important that metal ions such as of silver or the like act on the bacteria. That is, metal ions such as silver ions must elute out from the resin composition. However, it was so far difficult to have the silver present in the formed body of the antibacterial resin composition efficiently eluted out onto the surface of the formed body, and there remained a problem in that the silver compound present in the formed body could not be effectively utilized.

Besides, the eluted metal ions and, specifically, silver in the state of ions were unstable readily turning into metal silver or a silver compound, and the antibacterial effect could not be efficiently attained.

It is, therefore, an object of the present invention to provide an antibacterial resin composition which is excellent in economy and in antibacterial property, and uses a decreased amount of an expensive compound containing silver or the like as a result of permitting the metal such as silver having antibacterial power to efficiently elute out and the eluted metal to remain stable as metal ions.

Another object of the present invention is to provide an antibacterial resin composition having excellent antibacterial power not only in the initial stage of starting the use but even after the passage of time.

Means for Solving the Problems

According to a first aspect of the invention, there is provided an antibacterial resin composition comprising a thermoplastic resin or a thermosetting resin that contains a metal compound (hereinafter "metal compound (1)") represented by the following formula (1),

[Chemical 1]

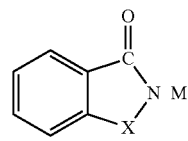

wherein M is any one of Ag, Cu, Zn, Co or Ni, and X is an atom selected from C, O, S and P, or an atomic group thereof.

In the above antibacterial resin composition, it is desired that the metal compound (1) is contained in an amount of 0.001 to 10 parts by weight per 100 parts by weight of the thermoplastic resin or the thermosetting resin.

According to a second aspect of the invention, there is provided an antibacterial resin composition comprising a thermoplastic resin or a thermosetting resin blended with at least one kind of fatty acid metal salt selected from Ag, Cu, Zn, Co and Ni, and a compound (hereinafter "compound (2)") represented by the following formula (2),

[Chemical 2]

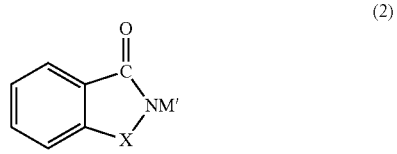

(2)

wherein M' is any one of Na, K or H, and X is an atom selected from C, O, S and P, or an atomic group thereof.

In the above antibacterial resin composition, it is desired that the fatty acid metal salt is contained in an amount of 0.001 to 10 parts by weight and the compound (2) is contained in an amount of 0.001 to 30 parts by weight per 100 parts by weight of the thermoplastic resin or the thermosetting resin.

According to a third aspect of the invention, there is provided an antibacterial resin composition comprising a thermoplastic and/or thermosetting resin blended with a metal-carrying compound carrying at least one kind of metal ions selected from Ag, Cu, Zn, Co and Ni, and the above compound (2).

In the above antibacterial resin composition, it is desired that the metal-carrying compound carrying the metal ions is contained in an amount of 0.001 to 10 parts by weight and the compound (2) is contained in an amount of 0.001 to 30 parts by weight per 100 parts by weight of the thermoplastic resin or the thermosetting resin.

According to the present invention, further, there is provided an antibacterial resin formed body obtained by mixing, heating and forming the above antibacterial resin composition.

Effects of the Invention

In the antibacterial resin composition according to the first aspect of the invention, the metal compound (1) has excellent oleophilic and hydrophilic properties. Therefore, the metal compound (1) has excellent affinity to the resin, disperses excellently in the resin and, therefore, metal ions such as of silver elute out onto the surface of the resin from the metal compound that is dispersed enabling antibacterial property to be efficiently exhibited.

In the antibacterial resin compositions of the second and third aspects of the invention, the thermoplastic resin or the thermosetting resin is blended with the compound (2) in combination with either at least one kind of fatty acid metal salt selected from group Ag, Cu, Zn, Co and Ni or a metal-carrying compound carrying at least one kind of metal ions selected from Ag, Cu, Zn, Co and Ni, making it possible to provide a resin formed body or a coating having the same antibacterial effect as that of when the metal compound (1) is directly added to the thermoplastic resin or the thermosetting resin.

That is, upon making the fatty acid metal salt or the metal-carrying compound present together with the compound (2) in the resin, metal ions eluted out from the fatty acid metal salt or the metal-carrying compound are allowed to stay together with the compound (2) maintaining stability; i.e., the metal ions and the compound (2) elute out simultaneously from the interior of the resin to exhibit excellent antibacterial property.

The antibacterial resin composition of the invention can effectively utilize the compound that contains metals such as silver and the like having antibacterial power. This makes it possible to decrease the amount of use of the compound that contains metals such as silver and the like, and offers advantage in economy.

Further, the resin composition makes it possible to efficiently utilize the metal compound (1), the compound (2) and the fatty acid metal salt or the metal-carrying compound that are present therein. In the initial period, the compound present on the surfaces exhibits antibacterial property and after the passage of time, the compound present inside the resin composition migrates onto the surfaces to exhibit antibacterial property enabling the antibacterial property to be exhibited over extended periods of time.

The above-mentioned action and effect of the antibacterial resin composition of the present invention will become obvious from the results of Examples described later.

That is, the films comprising the antibacterial resin compositions of the present invention (Examples 1 to 16) exhibit excellent antibacterial effect being blended with the compounds (compound (1) or compound (2) in combination with either the fatty acid metal salt or the metal-carrying compound) in amounts as specified, which could not be obtained to a sufficient degree with the films (Comparative Examples 1 to 20) comprising the resin compositions blended with silver stearate, phthalazone silver, benzotriazole silver, 1,8-naphthalimide silver or commercially available antibacterial agents. It is, therefore, obvious that silver ions are efficiently eluting out from the resin compositions of the present invention and excellent antibacterial property is being exhibited.

Further, the results of the Examples tell that the effect similar to the Examples is obtained by neither the phthalazone silver (Comparative Examples 7 to 10) nor the benzotriazole silver (Comparative Examples 11 to 14). It is, therefore, learned that in the present invention, a portion comprising a five-membered ring and a benzene ring in the metal compound (1) and the compound (2) is effective in stabilizing the silver ions, and that what is important to improve antibacterial property is to possess a heterocyclic ring comprising the five-membered ring and the five-membered ring having —CO—N—.

MODES FOR CARRYING OUT THE INVENTION (Metal Compounds (1))

As the concrete metal compounds represented by the above formula (1) and used in the first aspect of the invention, there can be exemplified the following ones though the invention is in no way limited thereto only. In the following formulas, Ag can be replaced by Cu, Zn, Co or Ni.

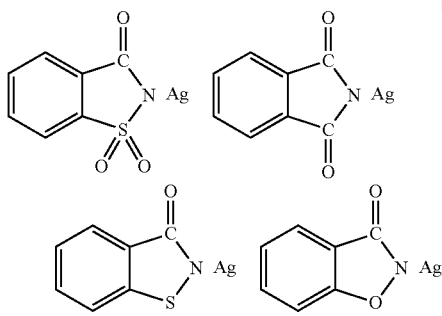

[Chemical 3]

Among the above compounds according to the present invention, saccharin silver can be preferably used.

Figure 1:
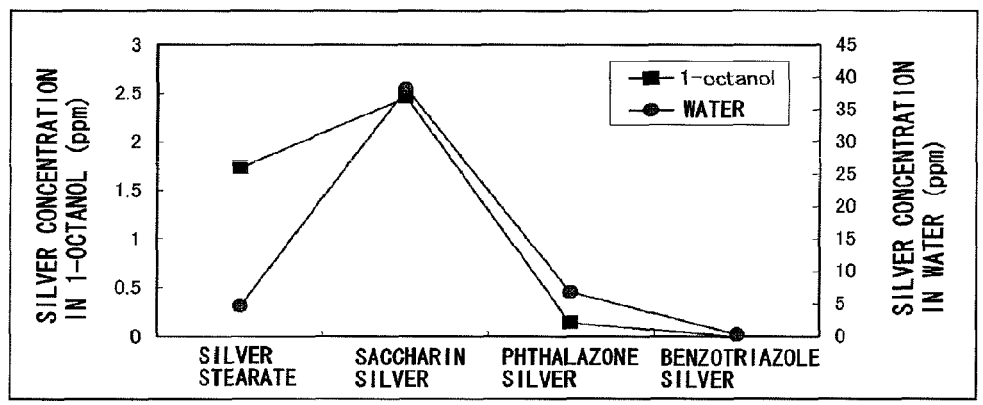
FIG. 1 is a diagram showing the measured results of the silver concentrations of the metal compounds.

FIG. 1 is a diagram showing the results of the silver concentrations of various silver-containing compounds eluted out in 1-octanol or in water as measured in compliance with the JIS Z 7260-107. The results tell that the saccharin silver has hydrophilic property and oleophilic property which are both superior to those of silver stearate, phthalazone silver or benzotriazole silver, and enables the antibacterial resin composition to exhibit excellent properties in agreement with the results of Examples that will appear later.

(Compounds (2))

As the compounds (2) represented by the above formula (2), there can be exemplified the following ones though the invention is in no way limited thereto only. In the compounds of the following formulas, Na can be replaced by K or H.

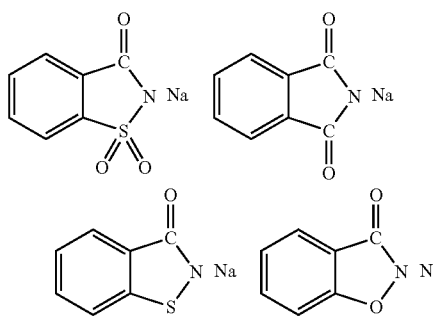

[Chemical 4]

In the present invention as described above, the saccharin silver is most suited as the metal compound (1). Therefore, the saccharin sodium, saccharin potassium or saccharin can also be favorably used for the above compound (2).

(Fatty Acid Metal Salts)

In the second aspect of the invention, the fatty acid metal salt used in combination with the compound (2) is a fatty acid metal salt of at least one kind of metal selected from Ag, Cu, Zn, Co and Ni. As the fatty acid, there can be exemplified myristic acid, stearic acid, oleic acid, palmitic acid, n-decanoic acid, paratoluic acid, succinic acid, malonic acid, tartaric acid, malic acid, glutaric acid, adipic acid, and acetic acid. Among them, the stearic acid can be favorably used. The most desired fatty acid metal salt will be the silver stearate.

Here, upon using the fatty acid metal salt and the compound (2) in combination, these two compounds may react with each other depending upon the kind of the fatty acid metal salt and the compound (2) that are used, and the compound (2) coordinates with a metal such as silver of the fatty acid metal salt to form the metal compound (1), permitting the silver ions to be stabilized and often making it possible to obtain the same constitution as that of when the metal compound (1) is directly coordinated.

(Metal-Carrying Compounds)

In the third aspect of the invention, the metal-carrying compound carrying metal ions used in combination with the compound (2) will be an inorganic ion exchanger or an inorganic adsorbent carrying metal ions of at least one kind of metal selected from Ag, Cu, Zn, Co and Ni.

The metal-carrying compound carrying metal ions by itself has, generally, been used as an antibacterial agent, and exhibits antibacterial action as the metal ions are eluted out. In the present invention, it is considered that the metal ions and the compound (2) together are made present in the resin accounting for the stable presence of metal ions, and that the metal ions and the compound (2) elute out simultaneously from the interior of the resin accounting for the exhibition of excellent antibacterial power.

As the inorganic ion exchanger, there can be exemplified zeolite, zirconium phosphate, potassium phosphate, solubilizable glass, magnesium silicate aluminate, calcium silicate, hydrotalcite and calcium apatite. As the inorganic adsorbent, there can be exemplified silica gel and active alumina. In the invention, however, zeolite and zirconium phosphate can be particularly preferably used.

(Thermoplastic Resins)

As the thermoplastic resin that can be used for the antibacterial resin composition of the invention, there can be used any known resins. For instance, there can be exemplified olefin resins such as low-, medium- or high-density polyethylene, linear low-density polyethylene, linear very-low-density polyethylene, isotactic polypropylene, syndiotactic polypropylene, propylene-ethylene copolymer, polybutene-1, ethylene-butene-1 copolymer, propylene-butene-1 copolymer, and ethylene-propylene-butene-1 copolymer; polyester resins such as polyethylene terephthalate, polybutylene terephthalate and polyethylene naphthalate; polyamide resins such as nylon 6, nylon 6,6, and nylon 6,10; and polycarbonate resins.

In the present invention, the polyethylene or polypropylene can be particularly preferably used.

(Thermosetting Resins)

As the thermosetting resin that can be used for the antibacterial resin composition of the invention, there can be used any known resins. For instance, there can be exemplified phenol resin, epoxy resin, urethane resin, melamine resin, urea resin, alkyd resin, unsaturated polyester resin and silicone resin.

In the present invention, the silicone resin can be particularly preferably used.

(Antibacterial Resin Compositions)

In the antibacterial resin composition according to the first aspect of the invention, the metal compound (1) is desirably used in an amount of 0.001 to 10 parts by weight and, specifically, 0.005 to 1 part by weight per 100 parts by weight of the thermoplastic resin or the thermosetting resin. If the amount of the metal compound (1) is smaller than the above range, the antibacterial effect is not obtained to a sufficient degree. The antibacterial effect can be enhanced by increasing the amount to be larger than the above range which, however, is not desirable from the standpoint of economy and formability.

Here, the antibacterial stands for a state where the multiplication of germs is suppressed on the surfaces of the products, and the antibacterial effect is the effect of the antibacterially-treated products as judged in terms of the antibacterially active value or the bacteriostatically active value stipulated under the JIS Z 2801 or the JIS L 1902.

In the antibacterial resin compositions according to the second and third aspects of the invention, the fatty acid metal salt or the metal-carrying compound is desirably used in an amount of 0.001 to 10 parts by weight and, specifically, 0.005 to 1 part by weight per 100 parts by weight of the thermoplastic resin or the thermosetting resin, and the compound (2) is desirably used in an amount of 0.001 to 30 parts by weight and, specifically, 0.02 to 10 parts by weight per 100 parts by weight of the thermoplastic resin or the thermosetting resin.

Depending on the use, further, the antibacterial resin composition of the present invention can be blended with various blending agents known per se., such as filler, plasticizer, leveling agent, viscosity-increasing agent, viscosity-decreasing agent, stabilizer, antioxidant, ultraviolet-ray absorber and pigment according to known recipe.

The antibacterial thermoplastic resin composition obtained by blending the thermoplastic resin with the metal compound (1) or with the combination of fatty acid metal salt or the metal-carrying compound and the compound (2), can be subjected to the known melt-forming relying on the two-roll-forming method, injection-forming method, extrusion-forming method or compression-forming method to produce antibacterial resin formed articles in shapes that meet the use as finally formed articles, such as granules, pellets, fibers, films, sheets, containers and the like.

The temperature for forming the resin formed articles may vary depending on the forming method or on the kind of the thermoplastic resin, metal compound (1), fatty acid metal salt, metal-carrying compound and compound (2) that are used, and cannot be definitely determined, but may be within a temperature range in which the thermoplastic resin that is used can be formed.

Further, the resin formed articles can be constituted by using the antibacterial thermoplastic resin composition of the invention alone but can also be constituted in a multi-layer structure by using any other resins in combination.

The antibacterial thermosetting resin composition obtained by blending the thermosetting resin with the metal compound (1) or with the combination of fatty acid metal salt or the metal-carrying compound and the compound (2), can be favorably used as coating material composition, coating agent or adhesive composition in a customary manner and can, further, be formed into resin articles such as films and sheets.

The heating and curing conditions for forming the coating or the resin formed articles may vary depending on the thermosetting resin, metal compound (1), or on the kind of the fatty acid metal salt or the metal-carrying compound and the compound (2) that are used, and cannot be definitely determined, but can be set based on the temperature and time for curing the thermosetting resin that is used.

EXAMPLES

Example 1

A homopolypropylene (F-704NP manufactured by Prime Polymer Co.) was blended with 0.01% by weight of saccharin silver and was extruded by using a biaxial extruder (manufactured by Toyo Seiki Seisaku-sho, Ltd.) at an extrusion forming machine setpoint temperature of 180° C. under a forming condition of Q (ejection amount)/N (screw revolving speed)=4/150=0.027 to prepare a film 100 μm in thickness.

Examples 2 to 4 and 7 to 16, Comparative Examples 1 to 20

Films were prepared in the same manner as in Example 1 but changing the kind of the silver compound and the amount of its addition as shown in Table 1. The antibacterial agent A in Table was the zirconium type antibacterial agent (trade name: Novaron (AQ1100) manufactured by Toa Gosei Co.).

Examples 5 and 6

A silicone resin (YSR3022 manufactured by Momentive Performance Materials Japan Godo Co.) was blended with the saccharin silver in amounts of 0.01% by weight or 0.1% by weight, and was diluted with toluene into about 5 times as a whole followed by mixing and stirring. Thereafter, a catalyst (YC6831 manufactured by Momentive Performance Materials Japan Godo Co.) was added thereto in an amount of 4% in terms of the weight of the silicone resin, and the mixture was left to stand still at 50° C. for 3 hours so as to be cured to thereby prepare silicone films.
(Method of Evaluation)

The antibacterial testing was carried out in compliance with the JIS Z 2801:2000 (Antibacterially Treated Products—Antibacterial Testing Method). The bacterial strain was *Staphylococcus aureus* (*S. aureus*). The antibacterially active value stands for a logarithmic value of a number obtained by dividing the number of bacteria cultivated on the untreated film by the number of bacteria cultivated on the antibacterially treated film.
(Judging the Antibacterial Effect)

The antibacterial effect was judged to be ○ when the antibacterially active value was not less than 2.0 with the amount of addition of both 0.1% by weight and 0.01% by weight. The antibacterial effect was judged to be Δ when antibacterially active value was not less than 2.0 with the amount of addition of 0.1% by weight but was less than 2.0 with the amount of addition of 0.01% by weight. The antibacterial effect was judged to be X when antibacterially active value was less than 2.0 with the amount of addition of both 0.1% by weight and 0.01% by weight.

TABLE 1

|  | Kind | Concentration (wt %) | Resin | Antibacterially active value | Judged |
| --- | --- | --- | --- | --- | --- |
| Ex. 1 | saccharin silver | 0.01 | PP | 4.9 | ○ |
| Ex. 2 | saccharin silver | 0.1 | PP | 4.9 | ○ |
| Ex. 3 | saccharin silver | 0.01 | PE | 4.9 | ○ |
| Ex. 4 | saccharin silver | 0.1 | PE | 4.9 | ○ |
| Ex. 5 | saccharin silver | 0.01 | silicone | 4.9 | ○ |

TABLE 1-continued

| | Kind | Concentration (wt %) | Resin | Antibacterially active value | Judged |
|---|---|---|---|---|---|
| Ex. 6 | saccharin silver | 0.1 | silicone | 4.9 | ○ |
| Ex. 7 | silver stearate + saccharin Na | 0.01 + 0.05 | PP | 2.2 | ○ |
| Ex. 8 | silver stearate + saccharin Na | 0.1 + 0.5 | PP | 4.9 | ○ |
| Ex. 9 | silver stearate + saccharin Na | 0.01 + 0.05 | PE | 4.9 | ○ |
| Ex. 10 | silver stearate + saccharin Na | 0.1 + 0.5 | PE | 4.9 | ○ |
| Ex. 11 | silver stearate + saccharin | 0.01 + 0.05 | PP | 4.9 | ○ |
| Ex. 12 | silver stearate + saccharin | 0.1 + 0.5 | PP | 4.9 | ○ |
| Ex. 13 | silver stearate + saccharin | 0.01 + 0.05 | PE | 4.9 | ○ |
| Ex. 14 | silver stearate + saccharin | 0.1 + 0.5 | PE | 4.9 | ○ |
| Ex. 15 | antibacterial agent A + saccharin | 0.1 + 0.5 | PP | 2.3 | ○ |
| Ex. 16 | antibacterial agent A + saccharin | 0.1 + 0.5 | PE | 4.5 | ○ |
| Comp. Ex. 1 | — | — | PP | 0 | X |
| Comp. Ex. 2 | — | — | PE | 0 | X |
| Comp. Ex. 3 | silver stearate | 0.01 | PP | 0.2 | X |
| Comp. Ex. 4 | silver stearate | 0.1 | PP | 1.4 | X |
| Comp. Ex. 5 | silver stearate | 0.01 | PE | 0.5 | Δ |
| Comp. Ex. 6 | silver stearate | 0.1 | PE | 4.9 | Δ |
| Comp. Ex. 7 | phthalazone silver | 0.01 | PP | 0 | X |
| Comp. Ex. 8 | phthalazone silver | 0.1 | PP | 0 | X |
| Comp. Ex. 9 | phthalazone silver | 0.01 | PE | 0.4 | Δ |
| Comp. Ex. 10 | phthalazone silver | 0.1 | PE | 2.2 | Δ |
| Comp. Ex. 11 | benzotriazole silver | 0.01 | PP | 0.2 | X |
| Comp. Ex. 12 | benzotriazole silver | 0.1 | PP | 0.8 | X |
| Comp. Ex. 13 | benzotriazole silver | 0.01 | PE | 0.4 | Δ |
| Comp. Ex. 14 | benzotriazole silver | 0.1 | PE | 2.2 | Δ |
| Comp. Ex. 15 | 1,8-naphthalimide silver | 0.01 | PP | 0 | X |
| Comp. Ex. 16 | 1,8-naphthalimide silver | 0.1 | PP | 0 | X |
| Comp. Ex. 17 | 1,8-naphthalimide silver | 0.01 | PE | 0.6 | X |
| Comp. Ex. 18 | 1,8-naphthalimide silver | 0.1 | PE | 0.6 | X |
| Comp. Ex. 19 | antibacterial agent A | 0.1 | PP | 0.5 | X |
| Comp. Ex. 20 | antibacterial agent A | 0.1 | PE | 0.2 | X |

As is obvious from Table 1, the films of the Examples exhibited antibacterial property even with 0.01% by weight of addition of the compounds. This is because the silver compound is homogeneously dispersed in the resin as described above and, as a result, silver is eluted out more efficiently than ever before and remains stable as silver ions. The films of the Comparative Examples, on the other hand, did not exhibit antibacterial property or needed the addition of 0.1% by weight of the compounds to exhibit the antibacterial property.

(Testing the Elution of Silver)

Figure 2:
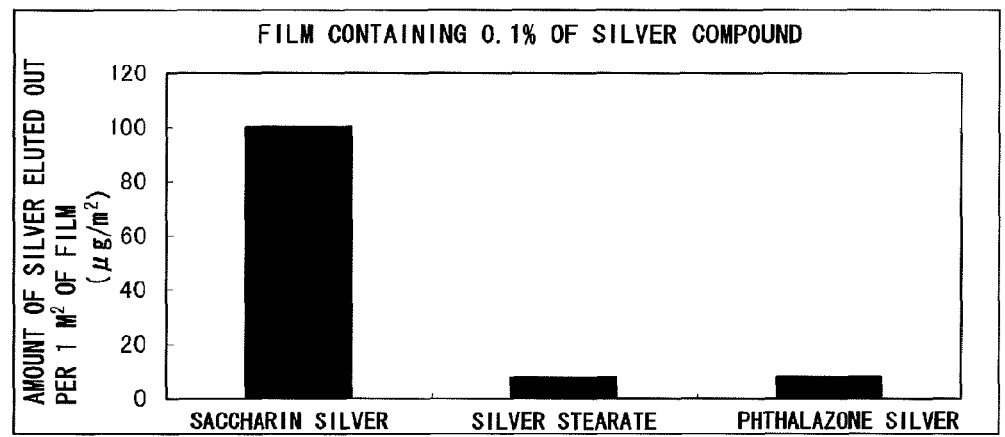
FIG. 2 is a diagram showing the measured results of the amounts of silver eluted out in Example 2 and Comparative Examples 4 and 8.

Films prepared in Example 2 and Comparative Examples 4 and 8 were tested for their elution of silver. Two pieces of films measuring 5 cm×25 cm were thrown into 50 ml of water, and were left to stand therein at 25° C. for 18 hours. Thereafter, by using an emission spectroscope (iCAP6500 manufactured by Thermo Scientific Co.), the water was measured for the amount of silver eluted therein. The measured results were as shown in FIG. 2 from which it was learned that the film containing the saccharin silver permitted silver to elute out more than the films containing the silver stearate or the phthalazone silver.

INDUSTRIAL APPLICABILITY

Despite of containing the metal compound capable of exhibiting antibacterial property, such as silver, in only small amounts, the antibacterial resin composition of the present invention is capable of efficiently exhibiting excellent antibacterial power, is advantageous in economy, and can be favorably used for the disposable products and products in general.

Further, the antibacterial resin composition of the present invention is capable of effectively inactivating not only bacteria, allergic substances, etc. but also true fungi, enzymes having specific stereo structures depending on the arrangement of amino acids, and microproteins such as viruses which are particulate substances comprising DNA or RNA (nucleic acid) and small numbers of protein molecules. The antibacterial resin composition can be used in the fields of, for example, medicine, daily commodities, bedclothes, building materials, electronic industries, water-treating facilities and the like. Concretely, the antibacterial resin composition can be favorably used for the products or medicinal articles used in the hospitals and the like, for the products used under high-temperature and highly humid conditions such as in a kitchen, bathroom, toilet, etc., as materials used in the houses, such as floor, wall, curtain, carpet, coating material for wall and floor, adhesive and joint mixture, as fiber products such as those used for the air conditioners, woven fabric and nonwoven fabric, and as filtering materials such as mask, filter and the like.

The invention claimed is:

1. A formed body, comprising
   a base body, and
   a coating layer formed on the base body,
   the coating layer is formed of an antibacterial resin composition prepared by blending
   at least one kind of fatty acid metal salt selected from Ag, Cu, Zn, Co and Ni, and a compound represented by the following formula (2):

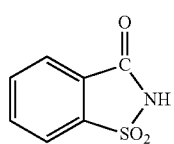
(2)

in a thermoplastic resin or a thermosetting resin selected from phenol resin, epoxy resin, urethane resin, melamine resin, urea resin, alkyd resin, or unsaturated polyester resin,
said fatty acid metal salt is contained in an amount of 0.001 to 10 parts by weight and said compound represented by formula (2) is contained in an amount of 0.001 to 30 parts by weight per 100 parts by weight of said thermoplastic resin or said thermosetting resin.

2. An antibacterial resin formed body obtained by mixing and heating
  a base body material and
  an antibacterial resin composition comprising
    at least one kind of fatty acid metal salt selected from Ag, Cu, Zn, Co and Ni,
    a compound represented by the following formula (2):

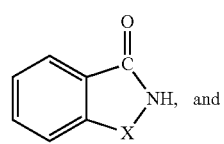
(2)

a thermoplastic resin or a thermosetting resin selected from phenol resin, epoxy resin, urethane resin, melamine resin, urea resin, alkyd resin, or unsaturated polyester resin;

wherein said fatty acid metal salt is contained in an amount of 0.001 to 10 parts by weight and said compound represented by formula (2) is contained in an amount of 0.001 to 30 parts by weight per 100 parts by weight of said thermoplastic resin or said thermosetting resin;

and then forming the antibacterial resin formed body.

* * * * *